| United States Patent [19] | [11] Patent Number: 4,822,601 |
| Goode et al. | [45] Date of Patent: Apr. 18, 1989 |

[54] COSMETIC BASE COMPOSITION WITH THERAPEUTIC PROPERTIES

[75] Inventors: Stephen T. Goode, Woodstock; Robert R. Linton, Crystal Lake, both of Ill.; Fred Baiocchi, Prairie Village, Kans.

[73] Assignee: R.I.T.A. Corporation, Crystal Lake, Ill.

[21] Appl. No.: 25,569

[22] Filed: Mar. 13, 1987

[51] Int. Cl.$^4$ .............................................. A61K 7/00
[52] U.S. Cl. ....................... 424/59; 424/69; 424/195.1; 514/54; 514/62; 514/506; 514/845; 514/886; 514/887; 514/870; 514/937; 514/943; 514/946; 514/947; 514/969
[58] Field of Search ............... 514/845, 887, 946, 947, 514/969, 54, 62, 506, 870, 886, 937, 943; 424/59, 69, 195.1

[56] References Cited

U.S. PATENT DOCUMENTS

| 4,036,991 | 7/1977 | Steifel | 514/786 |
| 4,184,978 | 1/1980 | France et al. | 514/943 |
| 4,379,755 | 4/1983 | Yamada et al. | 514/943 |
| 4,386,067 | 5/1983 | Guillon | 424/59 |

*Primary Examiner*—Morton Foelak
*Assistant Examiner*—Samuel A. Acquah
*Attorney, Agent, or Firm*—Marshall, O'Toole, Gerstein, Murray & Bicknell

[57] ABSTRACT

Cosmetic Base composition exhibiting therapeutic properties includes an acyl fatty acid lactylate ester or alkali metal salt thereof, a sucrose fatty acid ester, and a solvent.

25 Claims, No Drawings

COSMETIC BASE COMPOSITION WITH THERAPEUTIC PROPERTIES

FIELD OF THE INVENTION

The present invention relates generally to cosmetic base compositions and more particularly to an improved cosmetic base composition that exhibits unexpected utility as a pharmaceutical compound. The base composition of the present invention includes a therapeutically useful combination of two ingredients, wherein the first ingredient is an ester of a fatty acid or an alkali metal salt thereof, and the second ingredient is a sucrose fatty acid ester. The ester of a fatty acid used in the composition of the present invention may be a mono- or a poly- ester, preferably stearoyl lactylic acid or an alkali metal salt thereof. The sucrose fatty acid ester used in the composition of the present invention is preferably sucrose cocoate.

BACKGROUND OF THE INVENTION

The use of fatty acids, fatty acid salts and sucrose esters in cosmetic compositions and other dermatological compositions is known. Various fatty acids, fatty acid salts and sucrose esters have also been employed in pharmaceutical compositions, but never as the therapeutic ingredient.

Smith, U.S. Pat. Nos. 3,896,238, 4,150,114 and 4,046,886 disclose the use of a sucrose ester in combination with an alkyl sulfoxide or phosphine oxide in compositions for enhancing the penetration of pharmacologically active agents into the skin. Preferred sucrose esters include mono- and diacyl esters wherein the acyl substituents contain eight to twenty carbon atoms with sucrose monooleate the most preferred. Specifically disclosed are sucrose monooctanoate, sucrose monocaprate, sucrose monolaurate, sucrose monomyristate, sucrose monopalmitate, sucrose monostearate, sucrose monooleate, sucrose monoeicosanate, as well as the di- and tri-esters of the aforementioned compounds.

Japanese patent Jpn. Kokai Tokkyo Koho 81 75,437 discloses a composition which has utility as a base for a suppository containing a sucrose fatty acid ester displaying hydrophile-lypophile balance (HLB) value properties in the range of 1 to 5.

Kreps, U.S. Pat. No. 3,098,795 and Koulbanis, U.S. Pat. No. 4,422,952 disclose the utility of fatty acid esters as emulsifiers.

Sucrose fatty acid esters, and in particular, cocoates, have been used in detergent compositions. Brazilian patent Braz. Pedido PI No. 78 05,654 discloses a detergent composition containing sucrose coconut oil fatty acid mono- and di-esters useful as an effective soap in soft or hard water.

Japanese patent Jpn. Kokai Tokkyo Koho No. 75 29,608 discloses dishwashing detergent compositions containing a sucrose coconut oil fatty acid ester.

Sucrose fatty acid esters have also been used in the cosmetic industry. French patent 2,421,605 discloses a non-foaming cosmetic compound for cleaning the hair and scalp containing sucrose palmitate stearate.

Japanese patent Jpn. Kokai Tokkyo Koho No. 81 24,034 discloses an emulsion for a cosmetic cream containing sucrose fatty acid esters, preferably sucrose laurate.

Japanese patent Jpn. Kokai Tokkyo Koho No. 81 55,306 discloses cosmetic emulsions containing sucrose palmitate or sucrose stearate.

Marketing brochure, "Cosmetic Raw Materials", RITA corporation, p 5 (1985) and Technical Information Brochure PSE 141 G, RITA corporation, pp. 1-4 (9185), disclose the use of sucrose cocoate sold under the name of Grilloten for cosmetic use in body lotions, eye makeup removers, face cleansing creams, lotions, shampoos, foam bath products, liquid soaps, baby bath products, hair conditioners, cream rinses, and roll-on deodorants.

Lactylic mono fatty acid ester, in particular strearoyl lactylic acid and the sodium salt of this ester, has been used in compositions for cosmetic bases. Osipow, et al., *Fatty Acid Lactylates*, pp. 1-12 (1969) discloses that stearoyl lactylic acid and its sodium salt are used as a cosmetic gelling agent. He further discloses that capryl lactylate, sodium lauroyl lactylate and sodium stearoyl lactylate are non-toxic and that the first two compounds exhibit anti-microbial activity.

Osipow, Pat. No. 3,472,940, Kreps, Pat. No. 3,098,795, Lynch, Pat. No. 4,529,605, and Teng, Pat. No. 4,193,989 also disclose the use of fatty acid esters in cosmetic compositions.

Other uses of fatty acid esters are disclosed in Cannell, U.S. Pat. No. 4,301,820, which teaches its use in permanent waving compositions, and Cannell, Pat. No. 4,424,820, which teaches its use in hair straightening compositions.

Thompson, U.S. Pat. No. 2,733,252 discloses a process for preparation of the fatty acid esters of lactylic acid and slats thereof in a commercial environment. This disclosure alludes to the possible use of such esters as biologically active agents.

SUMMARY OF THE INVENTION

The present invention provides cosmetic base compositions adapted to topical application to animal tissue, said compositions having utility as skin conditioners and cleansers and capable of exhibiting such unexpected therapeutic properties as promoting wound healing, increasing total lipid synthesis, increasing thickness of epidermis layer, increasing cell proliferation, stimulating synthesis of glycosaminoglycans and reducing skin dryness.

The compositions of this invention comprises from about 0.1% to about 15% by weight of a sucrose fatty acid ester and from about 0.3% to about 455 by weight of acyl fatty acid lactylate ester or alkali metal salt thereof and from about 50% to about 99.6% polar solvent.

A preferred composition of this invention comprises from about 0.5% to about 5% by weight of a sucrose fatty acid ester and about 1.5% to about 15% by weight of an acyl fatty acid lactylate ester or alkali metal salt thereof and from about 80% to about 98% by weight of a suitable solvent, preferably polar.

A presently most preferred optimal composition of this invention comprises about 1% by weight sucrose fatty acid lactylate ester and about 3% by weight acyl fatty acid ester or alkali metal salt thereof and about 96% polar solvent.

The sucrose fatty acid ester component of compositions of the present invention ordinarily comprise a mixture of monoacyl and diacyl sucrose esters. Preferred sucrose fatty acid esters exhibit a hydrophilic/-lipophilic balance (HLB) of from about 8 to about 16 and preferably from about 10 to about 13. The sucrose fatty acid esters are preferably selected from the group consisting of sucrose cocoate, sucrose ricinoleate, sucrose laurate and sucrose stearate.

The acyl fatty acid or alkali metal acyl fatty acid salt component of compositions of the present invention is preferably selected from the group consisting of stearoyl lactylic acid, stearoyl lactyl lactylic acid, isostearoyl lactylic acid, isostearoyl lactyl lactylic acid, stearoyl lactylate, sodium stearoyl lactylate, stearoyl lactyl lactylate, sodium stearoyl lactyl lactylate, isostearoyl lactylate, sodium isostearoyl lactylate, isostearoyl lactyl lactylate, and sodium isostearoyl lactyl lactylate.

Solvents for use in compositions of the present invention may include water, glycerin, cetearyl alcohol or any other suitable solvent.

The present invention also unexpectedly provides an inexpensive emulsifying agent exhibiting penetration enhancing properties for use with other therapeutically active agents including shea butter. The unexpected independent therapeutic properties of the compositions of the present invention are demonstrable in histological as well as biochemical studies.

Compositions of the present invention, depending on formulation, ordinarily provide a white, creamy lotion, salve, or ointment which is greaseless, odorless and nontoxic.

DETAILED DESCRIPTION OF THE INVENTION

The present invention provides compositions useful as therapeutic agents comprising a unique combination of ingredients including at least one sucrose fatty acid ester and at least one acyl fatty acid lactylate ester or salt thereof. The preferred combinations include, (1) sodium stearoyl lactylate with sucrose cocoate and, (2) stearoyl lactylic acid with sucrose cocoate.

These compositions may be used alone or in combination with, for example, Shea Butter (SHEBU) which enhances the therapeutic effect of the composition of the present invention. While not intended to be limiting on the invention, it is presently believed that penetration of the Shea Butter through epidermal tissue may be facilitated by co-application compositions of the present invention.

The compositions of the present invention herein may also include various other agents and ingredients commonly employed in dermatological and cosmetic ointments and lotions. For example, thickening agents such as carboxymethyl cellulose, coloring agents and the like can be present in the compositions of the present invention for enhancing their aesthetic nature.

The following illustrative examples relating to formulations made in accordance with the present invention are intended to illustrate typical compositions are not intended to be limiting on the scope of the invention. All materials utilized in the formulations are commercially available.

EXAMPLE 1

| Formulation I | |
|---|---|
| Ingredient | Percent (by volume) |
| Sodium stearoyl lactylate (Pationic SSL) | 3% |
| Sucrose cocoate (Grilloten LSE 87K) | 1% |
| Water | 96% |

| Formulation II | |
|---|---|
| Ingredient | Percent (by volume) |
| Sodium stearoyl lactylate (Pationic SSL) | 3% |
| Sucrose cocoate (Grilloten LSE 87K) | 1% |
| Shea Butter (SHEBU) | 3% |
| Water | 93% |

Formulations I and II above were made utilizing accepted manufacturing procedures in the cosmetic industry. In Formulation II the primary emulsifyer, sodium stearoyl lactylate, and coemulsifyer, sucrose cocoate, were combined and then heated prior to the addition of heated Shea Butter. The molten mass was mixed and then allowed to cool to room temperature. Both Formulations I and II provided a white, creamy lotion, which was greaseless, odorless and nontoxic.

These formulations were tested at the College of Medicine, University of Arizona, to determine the morphology and biochemistry of the skin after topical administration of the formulations. More specifically, following topical administration to skin of test animals, skin samples were assays for alteration of skin thickness, and for variances in: (1) epithelial DNA synthesis as a measure of all proliferation; (2) glycosaminoglycan content; and, (3) lipid content.

TREATMENT PROTOCOL a total of 24 Sprague-Dawley male rats of 220 gram average body weight were anesthetized with 0.05 milliliters (ml) Innovar Vet by subcutaneous injection. The skin of the dorsum was closely shaved to expose a 4 by 6 centimeter area. The rats were evenly and randomly divided into experimental and control groups. One third received Formulation I treatment alone, one third received Formulation Ii treatment and one third received no treatment. A volume of 0.5 ml of Formulation I or Formulation II was evenly spread over the shaved skin and the area covered with a Tegaderm adhesive occlusion polyurethane film. The Tegaderm adhered to the edges of the shaved skin and formed a pocket preventing spreading or loss of the base from the application area.

The treatment was repeated every second day, a total of seven times, during a fourteen day treatment period. At the time of sacrifice, the skin from the shaved area was removed from all rats.

Procedure I: Effect of Topically Applied Formulations I and II on Skin Monophology This procedure was performed to determine if there was any change in thickness of the epidermis following treatment with Formulation I or Formulation II. One section of dissected skin was fixed for histology in Baker's formalin (10%). Skin histology analysis was performed on 5 micron thick sections of this sample that were strictly perpendicular to the surface plane of the skin. The slices were stained with hemotoxylin and eosin and analyzed at 160-fold magnification in a Zeiss Photomic III scientific microscope coupled to an RCA television screen camera. The thickness of the epidermis was measured by an IPM photoanalyzer whose signal was input into a video micrometer for digital micrometry. A summary of the results is set out in Table I and shows that the thickness of the epidermis increased significantly ($p<0.01$) in the test groups treated with Formulation I and Formulation II as compared to the untreated group controls. This was due to an increase in the number of cells as well as an increase in the size of the cells. There was not significant difference in epithelial thickness between the Formulation I and Formulation II-treated groups.

Procedure II. Measurement of Epithelial DNA Synthesis

The 100 mg thick skin slices were minced in 3 ml of Minimal Essential Media (MEM) with 20 μCi $H^3$-thymidine. The mixture was incubated for three hours at 37° C. and cooled to 4° C. The supernatant was discarded and the solid phase rinsed with 10 ml of cold saline and incubated with 3 ml of 1 N NaOH for 15 minutes (min) at 37° C. The solid phase was homogenized in a polytron and reincubated for 35 min at 37° C. and cooled to room temperature (R.T.). The addition of 1.5 ml of 2 N HCl neutralized the pH of the mixture which was subsequently cooled to 4° C. and an equal volume of 105 Trichloroacetic Acid (TCA) was added. The mixture was allowed to stand for 15 min at 4° C. Centrifugation for 10 min. at 2000 g produced a pellet. The supernatant was discarded and the pellet resuspended in 5 ml 5% TCA. This centrifugation step was repeated 3 times in order to remove any free H3-thymidine. The pellet was resuspended in 2.2 ml of 5% TCA and sonicated at maximum amperage for 30 seconds. One ml samples were diluted with 10 ml of aquasol and the radioactivity was counted. Digleman, et al., J. Surg. Res. 24, pp 45–51 (1978). The results of this procedure are set out in Table I.

Procedure III: Metabolic Labeling of Skin Glycosaminoglycans (GAG)

Skin tissue was weighed and finely chopped into approximately cubic millimeter pieces, transferred to incubation flasks and washed with saline. Five to ten ml of incubation medium consisting of MEM with the isotope, $H^3$-glucosamine present in a concentration of 10–15 μCi/ml media were added to the tissue. The flasks were placed in a 37° C. bath and incubated for 6 hours, then chilled. The tissue was washed with cold saline and homogenized by polytron. The homogenate pellet was resuspended in 0.1 M phosphate buffer, pH 8, containing 0.1 M Ethylene diamine Tetracetic Acid EDTA and incubated at 37° C. for approximately one hour to inactivate metallic enzymes. Papin, cysteine and HCl were added and the mixture incubated overnight at 60° C. The digest was dialyzed against $H_2O$, ethanol was added and the mixture let stand overnight at 4° C. The precipitate was recovered by centrifugation and the pellet dissolved in a small amount of water. Reprecipitation with cetylpyridinium chloride at room temperature overnight produced GAG. The sample was counted using standard techniques. [Original reference: Scott, J.E. Meth. Biochem. Anal. 8, pp. 145–197 (1960).] The results of this procedure are set out in Table I.

Procedure IV. Determination of In Vitro Lipogenesis

Skin slices were incubated in a sealed vial containing 4 μCi $C^{14}$-acetate for three hours at 37.8° C. in a total volume of 2 ml 0.1 M phosphate buffer (pH 7.4) in normal saline plus the coenzyme mixture of the following constitution:

| | |
|---|---|
| ATP | 5.0 μmoles |
| glucose-1-phosphate | 22.5 μmoles |
| glutathione | 30.0 μmoles |
| coenzyme A | 0.2 μmoles |
| NAD | 1.2 μmoles |
| NADP | 1.4 μmoles |
| magnesium chloride | 30.0 μmoles |

The reaction was stopped by freezing and the mixture lyophilized to dryness.

The lipid extraction was performed by the addition of 5 ml chloroform: methanol (2:1). Of this extract, 3 ml were transferred to open test tubes and washed twice with 3 ml aliquots of 1.0 M sodium acetate, and with 3 ml distilled water. The upper-phase was discarded after each washing. Methanol (2 ml) was added to the washed extract (lower phase). After agitation, 0.5 ml of the mixture was transferred to a counting vial. Ten ml of scintillation fluid was added and the sample was counted.

The remaining washed extract was taken to dryness at 50° C. under a continuous $N_2$ stream. Carrier lipids in chloroform: methanol (2:1) were added to the tubes and the total volume adjusted to 200 μl with chloroform: methanol (2:1). Eighty μl samples (40 μl per strip) were plated and developed on two sets of thin layer chromatography (TLC) plates.

The lipid spots were visualized under UV light following the spraying of the TLC plates with an ethanol solution containing 0.2% Rhodamine β. The spots corresponding to phospholipids and neutral lipids were scraped into counting vials, 2 ml acetic acid and 10 ml scintillation fluid were added and the radioactivity counted. Okabe, et al., Acta Medica Okayma 28, pp 403–410 (1974). Koblin, et al., Pharmacol & Exper. Therapeutics 211, pp 317–325, (1979). The results of these procedures are set out in Tables I and II.

TABLE I

THE EFFECT OF THE TREATMENT OF RAT INTACT SKIN WITH FORMULATION I AND FORMULATION II

| Parameter | Control no treatment | Formulation I | Formulation II |
|---|---|---|---|
| Epidermal layer thickness (microns) | 32.7 ± 4.5 | 132 ± 28 | 126 ± 36 |
| DNA synthesis $H^3$ thymidine $10^3$ × cpm/100 mg dry wt. | 225 ± 160.0 | 791 ± 580 | 1001 ± 529 |
| Total glycosaminoglycans $C^{14}$-glucosamine $10^3$ × cpm/g skin | 122 ± 36.0 | 263 ± 106 | 180 ± 42 |
| Total lipids $C^{14}$-acetate dpm/g skin | 3,691 ± 8,835 | 230,703 ± 29,273 | 301,652 ± 23,606 |

TABLE II

THE EFFECT OF THE TREATMENT OF RAT INTACT SKIN WITH FORMULATION I OR FORMULATION II SHEBU ON THE SYNTHESIS OF TOTAL AND VARIOUS SPECIES OF LIPIDS LIPID SYNTHESIS
DPM ($10^3$)/GRAM SKIN

| Parameter Studied | Control | Formulation I | Formulation II |
|---|---|---|---|
| Total Lipids | 83 ± 20 | 231 ± 80[1] | 302 ± 70 |
| Lysolecithin | 0.24 ± 0.1 | 0.48 ± 0.2[1] | 0.62 ± 0.2 |
| Sphyngomyelin | 0.11 ± 0.3 | 0.42 ± 0.3 | 0.41 ± 0.3 |
| Phosphatidylcholine | 2.2 ± 1 | 3.6 ± 1 | 6.0 ± 2 |
| Phosphatidylserine, phosphatidylinositol | 0.83 ± 0.2 | 1.8 ± 1[1] | 2.3 ± 0.8 |
| Phosphatidylethanolamine | 1.5 ± 1 | 2.8 ± 1 | 5.2 ± 2 |
| Phospholipids | 13 ± 8 | 35 ± 10[1] | 50 ± 30 |
| Cholesterol | 6.7 ± 4 | 16 ± 6[1] | 21 ± 9 |
| Fatty Acids | 11 ± 4 | 25 ± 5[1] | 27 ± 9 |
| Triglycerides | 12 ± 3 | 25 ± 10[1] | 30 ± 6 |
| Cholesterol ester | 19 ± 7 | 100 ± 40[1] | 150 ± 60 |

[1]Significantly different from control Group I variability is given by X ± SD

The results in Tables I and II show that cell proliferation was significantly increased over control values in the Formulation I-treated skin and Formulation II-treated skin. Glycosaminoglycan synthesis showed stimulation with much of the increase due to an increase in hyaluronic acid, the primary structural macromolecule in the dermis having the highest water binding capacity. The interest in hyaluronic acid is that an increase in water content in the cutaneous layers of the skin could correct for skin wrinkles on the surface. Total lipid synthesis also shows a significant increase.

The results of Procedures II, III and IV support the results in Procedure I and indicate that there is a genuine rejuvination effect exhibited following topical application of the formulations made in accordance with the present invention. There was an enhanced effect in DNA synthesis (cell proliferation) and lipogenesis with the Formulation II-treatment over Formulation I treatment alone. However, there was no significant difference between the groups in the measurement of glycosaminoglycan synthesis.

EXAMPLE 2

Additional tests were performed utilizing compositions of the present invention to determine their effect on wound healing.

Eighteen male Sprague-Dawley rats were shaved and prepped over the dorsal thoracic region. Six rats received Formulation I treatment, six received Formulation II treatment, and six received no treatment. A single 7-8 cm long midline "dermal deep" incision was made reaching deep fascia. After controlling the bleeding and washing blood clots from the wound, the skin was closed using staples. Daily treatments of Formulation I or Formulation II were applied liberally over the wound area. At the end of 17 days, the rats were sacrificed and the dorsal skin removed. Six to eight strips, 0.5 cm wide, were cut perpendicular to the wound axis. Wound breaking strength was measured on an Instron Tester, Model 1001 and histology specimens were taken randomly from each wound. The results of this experiment are contained in Table III.

TABLE III

EFFECT ON THE BREAKING STRENGTH OF RAT SKIN WOUNDS TREATED WITH FORMULATION I OR FORMULATION II

| Treatment | Number of Measurements | Breaking strength g/0.5 cm ± SEM |
|---|---|---|
| None, Control | 24 | 445.6 ± 22.9 |
| Formulation I | 37 | 656.4 ± 32.3 |
| Formulation II | 39 | 681.8 ± 38.0 |

The results in Table III show that treatment with compositions of the present invention increased healing as reflected in a significantly higher breaking strength of the skin specimens ($p < 0.01$). There was no significant difference between the breaking strength of the Formulation I-treated skin and the Formulation II-treated skin. Histology of Formulation I-treated skin or Formulation II-treated skin as compared to control skin showed more collagenation a thicker dermal layer at the site of skin incision, more capillaries in the repair tissue and a lack of skin surface defect.

EXAMPLE 3

An experiment was performed to determine the effect of treatment utilizing compositions of the present invention with and without occlusive bandage.

In this experiment the dorsal skin of three nude mice was treated with Formulation I or Formulation II for six hours by generous application, three mice received Formulation I treatment, three mice received Formulation II treatment and three mice were untreated. No dressing was utilized. A skin biopsy was taken at 6, 24, 48, 72, 96 and 120 hours after treatment. Specimens were prepared for histology and stained with hematoxylin-eosin. A second group of mice received a single treatment of Formulation I and another group treatment with Formulation II. All treated areas in these mice were occluded with impermeable Blenderm membrane left on the skin for 24 and 48 hours. At the end of each time period, skin biopsies were taken for histology. The results of these tests are set out in Table IV.

TABLE IV

| Group | Thickness of the epidermis (microns) | |
|---|---|---|
| | 24 hrs | 48 hrs |
| Control-intact skin no dressing | 27.3 ± 3.8 | — |
| Control-occlusive dressing only | 41.6 ± 9.1 | 38.7 ± 8.8 |
| Formulation I | 73.2 ± 10.2 | 76.2 ± 9.2 |
| Formulation II | 86.6 ± 9.4 | 82.1 ± 10.1 |

Variability given as X ± SD

The results set out in Table IV show that after six hours of the treatment without occlusion, no differences were observed between treated and untreated skin. However, treatment of the intact skin of nude mice for 24 or 48 hours under occlusive membrane significantly increased the thickness of the epidermal layer in both the Formulation I and Formulation II-treated skin.

EXAMPLE 4

Another formulation was made in accordance with the present invention and was tested to determine its effect on the sensitivity of rats skin to U.V. light.

| Formulation III | |
|---|---|
| Ingredient | Percent (by volume) |
| Stearoyl lactylic acid | 3% |
| Sucrose cocoate (Grilloten LSE 87K) | 1% |
| Water | 96% |

Formulation III was made utilizing the same manufacturing procedures used for Formulation I and II. Formulation III provided a white, creamy lotion, which was greaseless, odorless and non-toxic.

Six Sprague-Dawley male rats were pretreated with cod liver oil, 2 ml/rat for three days. They were anesthetized with 0.05 ml Innovar-Vet and a six by fifteen cm area on the dorsal surface was shaved and scrubbed with 70% ethanol. The rats were placed in restraining cages and exposed to UV light for 2.5 hours. Ethane excretion measurements were made at two, six, eighteen and twenty-four hours after UV light exposure using the method of Eskilson, et al. Dept. of Surgery, U. of Arizona, College of Medicine, Tucson, AZ. The method is based on the finding that radiation induces lipid peroxidation and peroxidation-related changes in the skin. Three rats were pretreated for three days with a cream containing 10% Formulation III. Three rats were untreated controls. The results are set out in Table V.

TABLE V

EFFECT OF TOPICAL APPLICATION OF FORMULATION III ON THE SENSITIVITY OF RAT SKIN TO ULTRAVIOLET LIGHT

| | Ethane Excretion (cumulative nano moles) Hours after treatment and UVL exposure | | | |
|---|---|---|---|---|
| Group | 2 | 6 | 18 | 24 |
| Control | $2.68 \pm 0.49$ | $2.36 \pm 1.70$ | $3.63 \pm 1.84$ | $4.64 \pm 0.78$ |
| Formulation III Treated | $0.00 \pm 0$ | $2.05 \pm 0.37$ | $2.10 \pm 0.26$ | $1.86 \pm 0.51$ |

Variability is given by $X \pm SD$, n = 3
Statistical significance tested by Student t-test The results showed a significant reduction in ethane excretion in rats treated with Formulation III indicating possible utility of the composition of the present invention as a sunscreen.

EXAMPLE 5

A further experiment was performed to determine the effect on epithelialization of the composition of the present invention. In this experiment pigs were wounded in a standard split thickness model. Two types of wound dressing coverages were compared with Duoderm®, a commercial product to determine their effect on epithelialization of the wound. Gauze, Formulation II soaked gauze and Duoderm were administered sterile and dry onto the wound. The dressings were left on the wound for 60 hours. The results are set out in Table VI.

TABLE VI

EVALUATION OF VARIOUS DRESSING MATERIALS ON THE RATE OF EPITHELIALIZATION OF STANDARD SPLIT THICKNESS WOUND IN PIGS

| Group | % Epithelialization |
|---|---|
| gauze | $74.5 \pm 11.6$ |
| FORMULATION II | $89.7 \pm 11.1$ |
| Duoderm | $91.6 \pm 7.1$ |

Data presented as $X \pm SD$. There were 24 determinations made in each group. Statistical evaluation and Duncan's multiple range test, the results at 95% confidence limit are shown below.

The results show a significant increase in the rate of epithelialization with the Duoderm-treated and Formulation II-treated animals.

Examples 1-5 demonstrate the unexpected therapeutic properties of the compositions of the present invention. Topical application of either Formulation I, Formulation II or Formulation III shows significant dermatological rejuvinative and protective properties as demonstrated in histological, as well as, biochemical studies. Histological examination of experimental tissue showed that animal skin treated with Formulation I or Formulation II shows a significant increase in the thickness of the epidermis, as well as, a mild increase in keratinocytes and fibroblasts. Wound healing was accelerated. Assays designed to measure an increase in biochemical activity reinforced these observations. Increased total lipid synthesis, DNA synthesis, and glycosaminoglycan synthesis suggested a rejuvenation effect. The results of treatment with Formulation I, Formulation II or Formulation III on animal skin indicate a healthier and less dry skin which heals faster in response to injury. Also, application of Formulation I or Formulation III decreases sensitivity to U.V. light, thus exhibiting utility as a sunscreen agent. When SHEBU is used in conjunction with Formulation I, an enhanced therapeutic effect is observed and is expected to be observed when used with Formulation III. For example, increased DNA synthesis and increased lipogenesis was demonstrated with use of Formulation II compared to use of Formulation I alone. This enhancement effect, however, does not demonstrate itself on the histological level. Treatment with Formulation I or Formulation II produced the same increase in epithelial thickness and acceleration of wound healing. No significant difference was demonstrated between the two groups.

The following formulations in accordance with the present invention were made using standard cosmetic manufacturing procedures.

| | Series I | | | | | |
|---|---|---|---|---|---|---|
| | Percent (by Volume) | | | | | |
| Ingredient | A | B | C | D | E | F |
| Sucrose Cocoate (Grilloten LSE 87K) | 1 | 2 | 4 | 8 | 3 | 12 |
| Stearoyl Lactylic Acid | 3 | 6 | 12 | 24 | 1 | 4 |
| Water | 96 | 92 | 84 | 68 | 96 | 84 |

| | Series II | | | | | | | | | |
|---|---|---|---|---|---|---|---|---|---|---|
| | Percent (by Volume) | | | | | | | | | |
| Ingredient | A | B | C | D | E | F | G | H | I | J |
| Sucrose Cocoate (Grilloten LSE 87K) | 1 | 1 | 1 | 1 | 8 | 16 | 1 | 2 | 4 | 8 |
| Stearoyl Lactylic Acid | 3 | 3 | | 3 | 24 | 48 | | | | |
| Water | | | | | | | 96 | 92 | 84 | 68 |
| Propylene Glycol | 96 | 96 | | | | | | | | |

-continued

| | Series II | | | | | | | | | |
|---|---|---|---|---|---|---|---|---|---|---|
| | Percent (by Volume) | | | | | | | | | |
| Ingredient | A | B | C | D | E | F | G | H | I | J |
| Glycerin | 96 | | | | | | | | | |
| Sodium Stearoyl Lactylate | | 3 | | | | | 3 | 6 | 12 | 24 |
| Cetearyl Alcohol | | | 96 | 68 | 36 | | | | | |

| | Series III | | | |
|---|---|---|---|---|
| | Percent (by Volume) | | | |
| Ingredient | A | B | C | D |
| Sucrose Cocoate 40% (Crodesta SL 40) | 1.4 | 1.4 | | |
| Stearoyl Lactylic Acid | 3 | | | 75 |
| Sodium Stearoyl Lactylate | | 3 | 75 | |
| Water | 95.6 | 95.6 | | |
| Sucrose Cocoate (Grilloten LSE 87K) | | | 25 | 25 |

All formulations combined easily. The formulations utilizing primary emulsifiers and coemulsifiers exhibited acceptable stability. All formulations provided a white, creamy lotion which was greaseless, odorless and nontoxic.

Useful as a replacement for (or adjunct to) sodium stearoyl lactylate in compositions of the invention is the sodium salt of an acyl lactic acid or acyl monohydroxy monocarboxylic acid as well as the sodium salts of palmitoyl lactylic acid, stearoyl lactyl lactylate, and the calcium salts of stearoyl lactylate and stearoyl-2-lactylate.

Useful as a replacement for (or adjunct to) sucrose cocoate in compositions of the invention are sucrose laurate, sucrose ricinoleate and sucrose stearate. These sucrose fatty acid esters all exhibit a hydrophilic/lipophilic balance between 8 and 16.

From the foregoing it is seen that compositions of the present invention exhibit a wide variety of highly desirable therapeutical and cosmetic base properties. The formulations disclosed in the examples may be varied dependent on the particular application, user and the like.

What is claimed is:

1. A composition for use as a therapeutic agent comprising about 1% to about 15% by weight sucrose fatty acid ester, about 3% to about 45% by weight acyl fatty acid lactylate ester or alkali metal salt thereof, and a solvent.

2. The composition in claim 1 wherein the sucrose fatty acid ester is sucrose cocoate.

3. The composition of claim 1 wherein the acyl fatty acid lactylate ester is stearoyl lactylic acid.

4. The composition of claim 1 wherein the acyl fatty acid lactylate ester salt si sodium stearoyl lactylate.

5. The composition of claim 1 wherein the ratio of acyl fatty acid ester to sucrose fatty acid lactylate ester ester is about 3 to 1.

6. The composition as in claim 1 wherein the acyl fatty acid is selected from the group consisting of: stearoyl lactylic aid, stearoyl lactyl lactylic acid, isostearoyl lactylic acid, and isostearoyl alctyl lactylic acid.

7. A composition as in claim 1 wherein the acyl fatty acid lactylate ester salt is selected from the group consisting of: the alkali metal salts of stearoyl lactylate, stearoyl lactyl lactylate, isostearoyl lactylate, and isostearoyl lactyl lactylate.

8. A composition as in claim 1 wherein the solvent is a polar solvent selected from the group consisting of: water and glycerin.

9. A composition as in claim 1 wherein the solvent is cetearyl alcohol.

10. A composition as in claim 1 wherein the sucrose fatty acid ester is selected from the group consisting of: sucrose ricinoleate, sucrose laurate, and sucrose stearate.

11. A composition as in claim 1, wherein the sucrose fatty acid ester has a hydrophilic/lipophilic balance from about 8 to about 16.

12. A method for enhancing healing of injured skin comprising applying thereto an effective amount of a composition comprising about 1% to about 15% by weight sucrose fatty acid ester, about 3% to about 45% by weight acyl fatty acid lactylate es5ter or alkali metal salt thereof, and a polar solvent.

13. A composition for use as a cosmetic base comprising about 1% to about 15% by weight sucrose cocoate, about 3% to about 45% by weight acyl fatty acid lactylate ester or alkali metal salt thereof, and a solvent.

14. The composition of claim 13 wherein the acyl fatty acid lactylate ester is stearoyl lactylic acid.

15. The composition of claim 14 wherein the acyl fatty ester salt is sodium stearoyl lactylate.

16. A composition for use as a therapeutically active agent comprising about 1% to about 15% by weight sucrose fatty acid ester, about 3% to about 455 by weight acyl fatty acid lactylate ester or alkali metal salt thereof, about 3% to about 45% Shea Butter and a solvent.

17. The composition in claim 16 wherein the sucrose fatty acid ester is sucrose cocoate.

18. The composition of claim 16 wherein the acyl fatty lactylate ester is stearoyl alctylic acid.

19. The composition of claim 16 wherein the acyl fatty acid lactylate salt is sodium stearoyl lactylate.

20. The composition as in claim 16 wherein the acyl fatty acid is selected from the group consisting of: stearoyl lactylic acid, stearoyl lactyl lactylic acid. isostearoyl lactylic acid, and isostearoyl lactyl lactylic acid.

21. A composition as in claim 15 wherein the acyl fatty acid lactylate ester salt is selected from the group consisting of the alkali metal salts of: stearoyl lactylate, stearoyl lactyl lactylate, isostearoyl lactylate, and isostearoyl lactyl lactylate.

22. A composition as in claim 16 wherein the solvent is a polar solvent selected from the group consisting of: water and glycerin.

23. A composition as in claim 16 wherein the solvent is cetearyl alcohol.

24. A composition as in claim 16, wherein the sucrose fatty acid ester has a hydrophilic/lipophilic balance from about 8 to about 16.

25. A method for enhancing healing of injured skin comprising applying thereto an effective amount of a composition comprising about 1% to about 15% by weight sucrose fatty acid ester, about 3% to about 45% by weight acyl fatty acid lactylate ester or alkali metal salt thereof, about 3% to about 45% Shea Butter and a solvent.

* * * * *

UNITED STATES PATENT AND TRADEMARK OFFICE
CERTIFICATE OF CORRECTION

PATENT NO. : 4,822,601
DATED : April 18, 1989
INVENTOR(S) : Stephen T. Goode, Robert R. Linton, Fred Baiocchi It is certified that error appears in the above-identified patent and that said Letters Patent is hereby corrected as shown below:

In column 2, line 33, change "slats" to "salts".

In column 5, line 34, change "H3" to "$H^3$".

In column 11, line 57, change "si" to "is".

In column 11, line 64, change "alctyl" to "lactyl".

In column 12, line 19, change "es5ter" to "ester".

In column 12, line 32, change "455" to "45%".

In column 12, line 39, change "alctylic" to "lactylic".

Signed and Sealed this

Twenty-eighth Day of November 1989

Attest:

JEFFREY M. SAMUELS

Attesting Officer     Acting Commissioner of Patents and Trademarks